United States Patent

Benner, Jr.

[11] Patent Number: 4,720,636
[45] Date of Patent: Jan. 19, 1988

[54] DROP DETECTING SYSTEM WHICH OPERATES UNDER DIFFERENT AMBIENT LIGHT CONDITIONS

[75] Inventor: James D. Benner, Jr., Sugarland, Tex.

[73] Assignee: Abbott Laboratories, North Chicago, Ill.

[21] Appl. No.: 30,276

[22] Filed: Mar. 23, 1987

Related U.S. Application Data

[63] Continuation of Ser. No. 637,933, Aug. 6, 1984, abandoned.

[51] Int. Cl.[4] .................... A61M 5/16; G01N 21/85
[52] U.S. Cl. ........................ 250/573; 128/DIG. 13; 340/606; 604/31; 604/246
[58] Field of Search ............ 250/573, 574, 222.1, 250/222.2, 214 B; 128/DIG. 13; 340/606, 608, 609; 604/31, 246

[56] References Cited

U.S. PATENT DOCUMENTS 3,867,628  2/1975  Brown .......................... 250/214 B
4,038,982  8/1977  Burke et al. ..................... 250/573
4,321,461  3/1982  Walter, Jr. et al. ............... 340/609
4,490,140  12/1984 Carr et al. ....................... 604/31

Primary Examiner—Edward P. Westin
Attorney, Agent, or Firm—Janet K. Hochstetler; Martin L. Katz

[57] ABSTRACT

A drop detecting system has light emitting diodes and phototransistors located on either side of a translucent drip chamber. The phototransistors respond to either the shadow or the reflection from a drop falling through a light beam produced by the light emitting diodes. The electrical response from the phototransistors is conducted to an integrator circuit which generates an electrical signal voltage. A comparator circuit receives the electrical signal voltage from the integrator circuit and outputs a signal indicating the presence of a drop passing through the drip chamber. A drip chamber housing cooperates with the drip chamber to shroud the translucent portion of the drip chamber. Additionally the drip chamber housing provides for the mounting of the light emitting diodes and the phototransistors.

8 Claims, 7 Drawing Figures

DROP DETECTING SYSTEM WHICH OPERATES UNDER DIFFERENT AMBIENT LIGHT CONDITIONS

This is a continuation of U.S. application Ser. No. 637,933 filed on Aug. 6, 1984 in the name of the same inventor named as inventor herein, now abandoned.

BACKGROUND OF THE INVENTION

The field of this invention relates to optical drop detecting systems. More specifically this invention relates to optical drop detecting systems which produce an electrical signal in response to a drop falling through a translucent drip chamber.

Optical drop detecting systems are commonly used with intravenous fluid administration equipment and enteral feeding apparatus. These optical drop detecting systems normally include a translucent drip chamber on which is mounted optical sensing apparatus. Optical sensing of the passage of a drop through the translucent drip chamber is typically performed by the interruption of a light beam by the falling drop. To accomplish this optical sensing a light source and receiver are positioned on either side of the translucent drip chamber. When the light beam produced by the light source is interrupted by the falling drop an electrical pulse is transmitted to recording equipment by the receiver. If the drop size is known the volume and flow rate of the monitored fluid can be measured by recording and counting the falling drops.

Problems have arisen in the operation of drop detecting systems when the optical sensing equipment is used in an environment with changing levels of ambient light. In such situations light receivers may become flooded with light and will not be able to detect the interruption of the light beam by the falling of the drop. Additionally, flashes or intermittent periods of darkness may trigger the same response as a falling drop. Such changing ambient light conditions may be present in a hospital room if the drop detecting system is located near a window or a lamp. The consequence of the recording of false signals will be improper and inaccurate administration of I.V. fluid or enteral feeding solutions to the patient.

Another problem for conventional drop detecting systems occurs when the drip chamber is inadvertently tilted from a vertical axis. This tilting of the drip chamber will cause the falling drops to land on one side of the drip chamber and possibly miss the optical sensing equipment entirely.

There is therefore a need in the art to provide a drop detecting system which is operable in a wide variety of constant or changing ambient light conditions. Additionally, there is also a need in the art to provide a drop detecting system that can be operated when the drip chamber is tilted from a vertical axis.

It is an advantage of the device of the present invention to provide a drop detecting system which is operable in a wide range of constant or changing ambient light conditions and is also operable whenever the drip chamber is tilted from a vertical axis.

SUMMARY OF THE INVENTION

A drop detecting system is provided that is used with a translucent drip chamber.

Optical sensing equipment consisting of light emitting diodes and phototransistors located on either side of the translucent drip chamber which produce an electrical response to each falling drop. When a drop falls, the light emitting diodes cause either a shadow or reflection to fall upon a phototransistor. The electrical response of the phototransistors is a change in conductivity directly dependent on the amount of light energy impacting on its surface. When the amount of light energy impacting on the surface of the phototransistor is reduced, as in the occasion of a shadow, the change in conductivity of the phototransistor will cause an electrical voltage pulse representing reduced conductivity to be passed by the phototransistor. In the case of a reflection of light energy from a falling drop onto the surface of a phototransistor, an excess of light energy will impact on the surface of the phototransistor. This excess of light energy will cause an increased conductivity of the phototransistor thereby allowing an electrical pulse representing increased conductivity to be passed by the phototransistor. An integrator circuit receives the electrical voltage pulses passed by the phototransistors in response to either a shadow or a reflection from the falling drop. The integrator circuit produces an electrical signal voltage in response to the electrical voltage pulse. The electrical signal voltage from the integrator circuit is conducted to a comparator circuit where it is compared to a reference electrical voltage. If the electrical signal voltage from the integrator circuit is greater than the reference electrical voltage, a signal output will be generated by the comparator circuit and conducted to a microprocessor which will record and count the number of drops which have fallen through the translucent drip chamber during a predetermined interval of time.

To assure accurate operation and location of the light emitting diodes and the phototransistors a housing is provided for the translucent drip chamber. The housing is formed to substantially shroud the translucent drip chamber and cooperate with a shade on the drip chamber to minimize the effect of ambient light on the optical sensing of falling drops by the drop detecting system of the present invention.

BRIEF DESCRIPTION OF THE DRAWINGS

A better understanding of the device of the present invention may be had by reference to the drawings wherein.

DETAILED DESCRIPTION OF THE PREFERRED EMBODIMENTS

Figure 1:
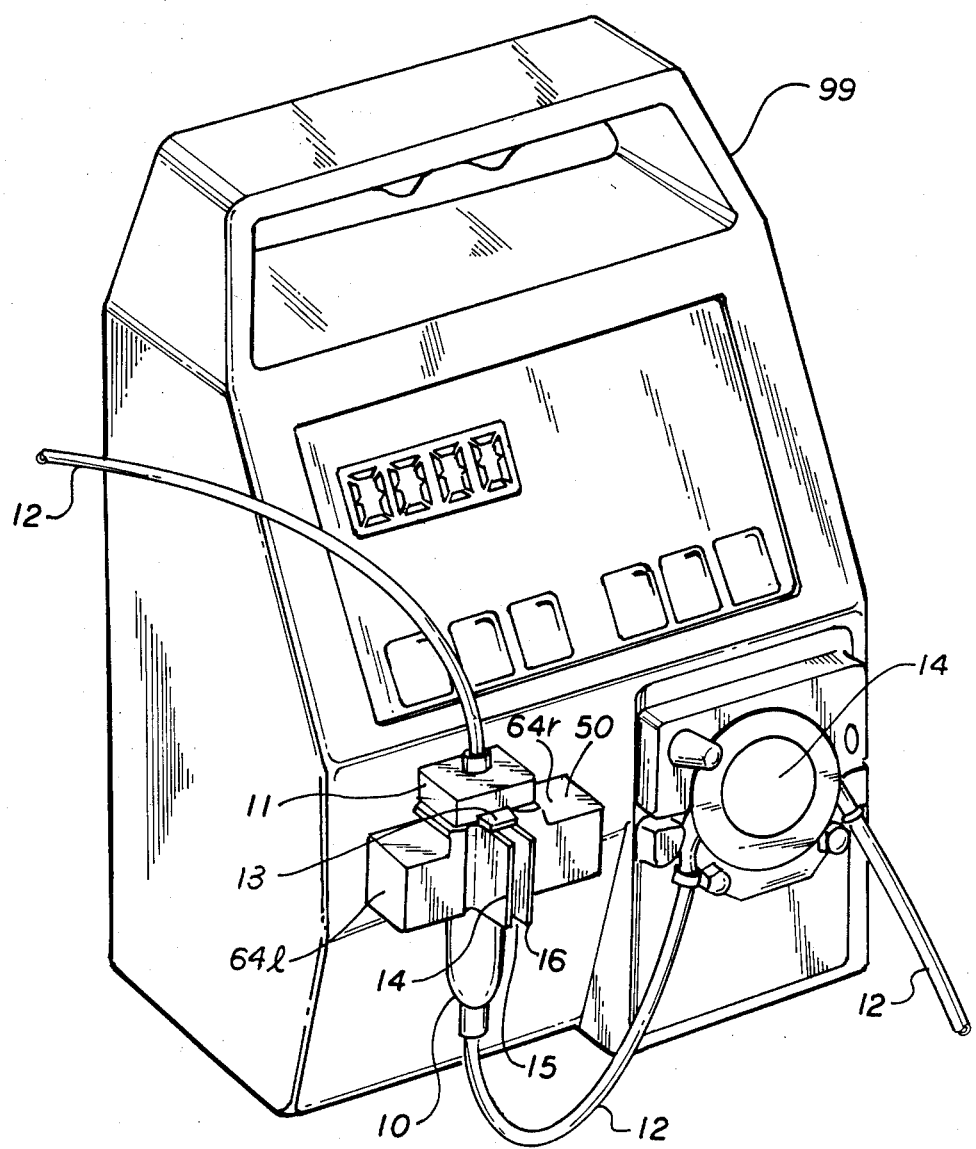
FIG. 1 is a perspective view of a flow control device which incorporates the drop detecting system of this invention.

In FIG. 1 translucent drip chamber 10 with opaque cap 11 is shown in operative association with a housing 50 which is located on flow control device 99. Flow control devices are typically used in enteral feeding or I.V. administration systems and employ pumps which may be of the syringe or peristaltic type. A peristaltic pump 14 is shown in FIG. 1. Flexible tubing 12 is connected to either end of translucent drip chamber 10. It will be noted that when translucent drip chamber 10 is mounted within housing 50 shade portion 12 of opaque cap 11 is operatively associated with housing 50 to assist in blocking ambient light from entry into the interior of housing 50. Additionally shutters 14 and 16 protrude from housing 50 to further block ambient light from the interior of housing 50.

Figure 7:
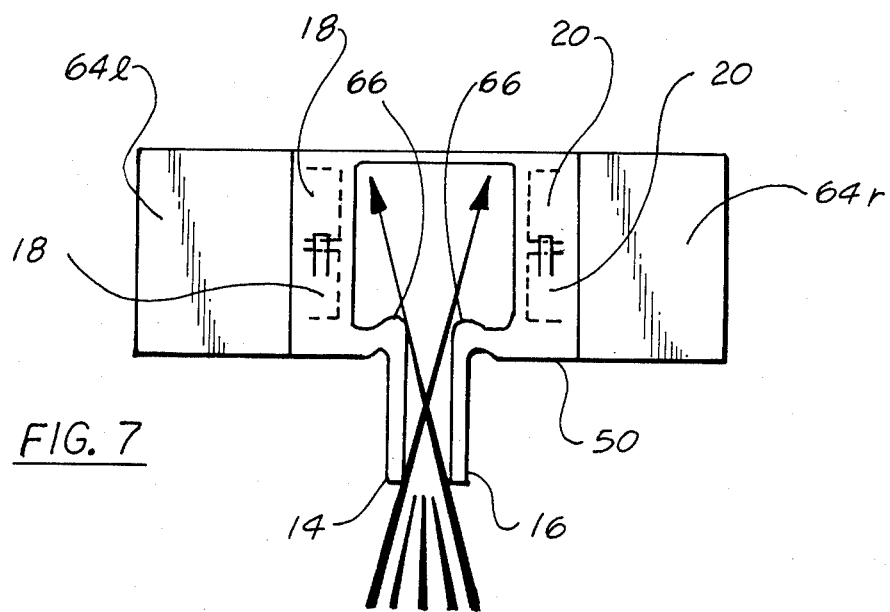
FIG. 7 is a top view of the housing shown in FIG. 6.

As can be best seen in FIG. 7, located within left side 64l of housing 50 are light emitting diodes 18 which emit light energy when electrically energized. Located on right side 64r of housing 50 are phototransistors 20 which are selected to be sensitive to the frequencies of light energy emitted by light emitting diodes 18. It will be understood that either the left side or right side may be chosen as long as diodes 18 are on one side and phototransistors 20 are on the other side.

Operation

Drip chamber 10 is placed in housing 50 by holding drip chamber 10 above housing 50 and allowing tubing 12 to pass through passageway 15 into space 62. From this position opaque cap 11 of drip chamber 10 may now be seated on upper surface 72 of housing 50. When the pump 14 (FIG. 1) is activated drops will begin to pass through translucent drip chamber 10. A drop former (not shown) contained within drip chamber 10 will assure that the drops are uniform in size and of a known volume. As each drop falls through drip chamber 10 one of the responses shown in FIGS. 2 and 3 will occur.

Figure 2:
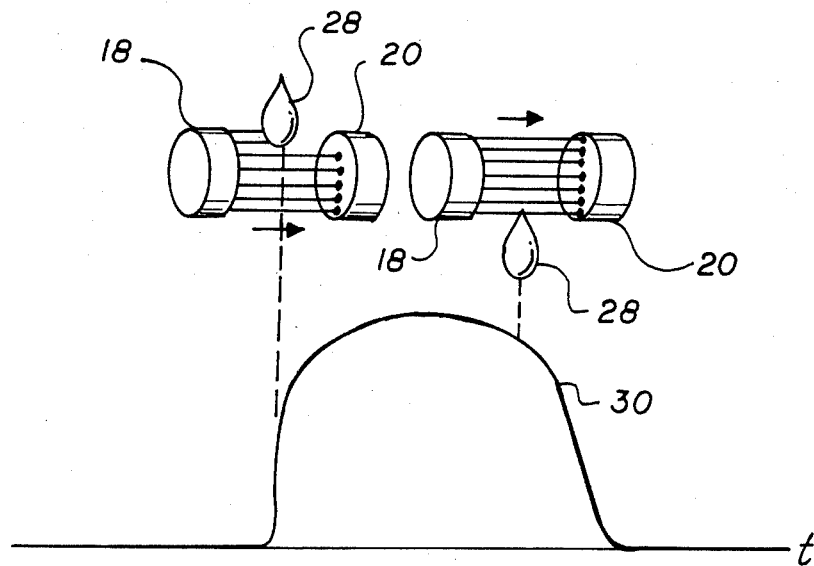
FIG. 2 is a schematic of system response in a low or normal ambient light condition.

FIG. 2 represents the situation with a low or normal level of ambient light. The falling drop 28 will cause a shadow to fall on phototransistor 20 which is located on the opposite side of drip chamber 10 from light emittor 18. The shadow falling on the surface of phototransistor 20 will cause reduced conductivity of phototransistor 20. This reduced conductivity will result in a positive voltage pulse 30 be allowed to pass through phototransistor 20.

Figure 3:
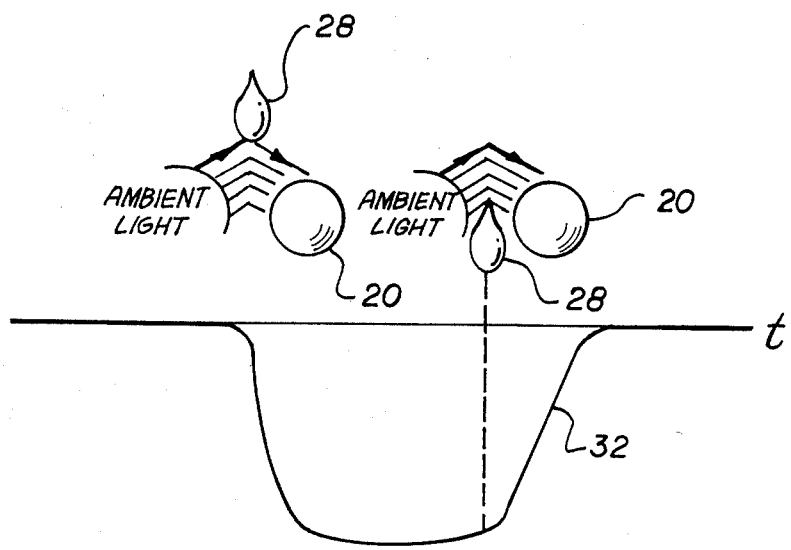
FIG. 3 is a schematic of system response in a high ambient light condition.

FIG. 3 represents the situation with a high level of ambient light. The falling drop 28 will reflect ambient light of the surface of a falling drop 28 to phototransistor 20. This resulting increase in light energy falling on the surface of phototransistor 20 will cause increased conductivity of phototransistor 20. This increased conductivity will result in a negative voltage pulse 32 be allowed to pass through phototransistor 20. The use of two emitters 18 and two phototransistors 20 to sense presence of a drop in translucent drip chamber 10 provides an added benefit. If drip chamber 10 is tilted right or left from a vertical axis, by up to twenty degrees in the preferred embodiment, the presence of a falling drop will still be detected. This performance, even when tilted, is obtained because the two light emitters 18 and the two phototransistors 20, completely cover the interior 62 of housing 50 (FIG. 7).

Figure 4:
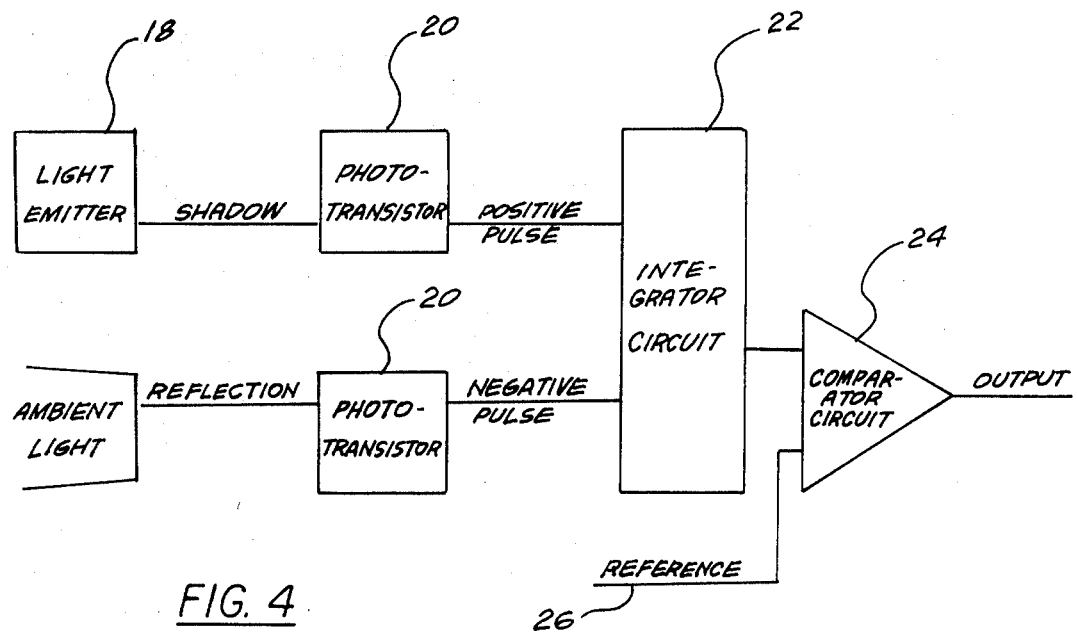
FIG. 4 is a block diagram of signal processing within the present invention.

Once the presence of a falling drop has produced a voltage pulse from phototransistors 20 the pulse is processed as shown in FIG. 4. Specifically, the output from the phototransistors 20, either a positive pulse 30 (FIG. 2) or negative pulse 32 (FIG. 3), will be received by integrator circuit 22 which will produce an electrical signal voltage which is then conducted to comparator 24. Comparator 24 will output a signal indicating the falling of a drop if the input from integrator circuit 22 is greater than a reference voltage 26.

Figure 5:
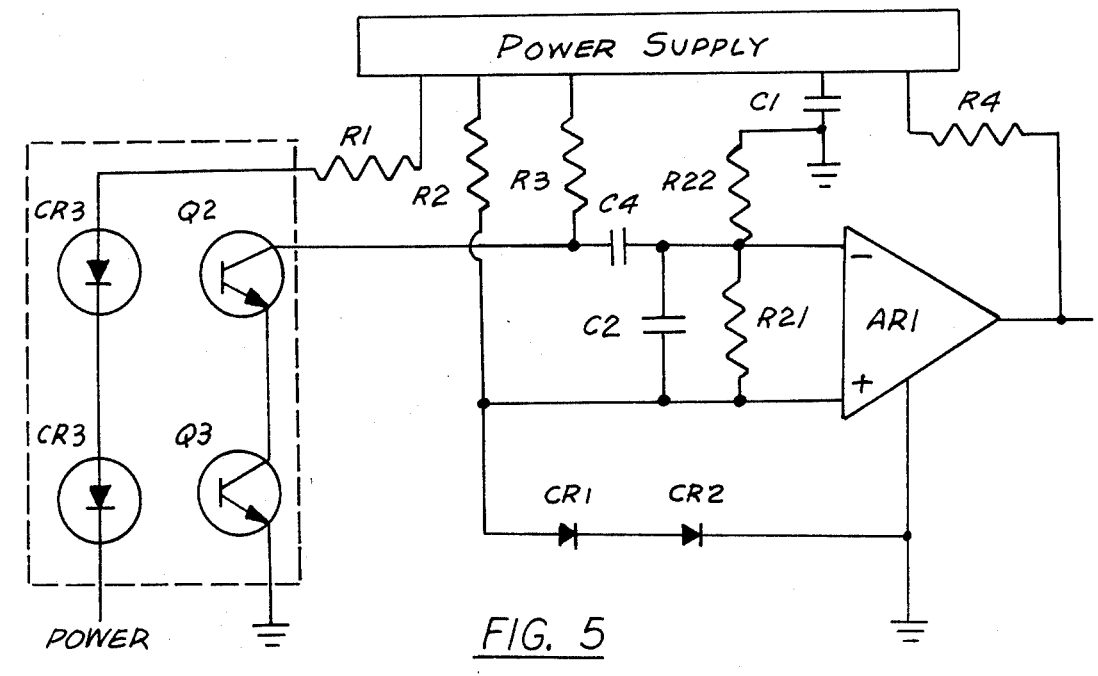
FIG. 5 is a schematic diagram of the electrical circuitry of the present invention.

The electrical circuitry which effects the signal processing shown in FIG. 4 are illustrated in FIG. 5. The proper output of series-connected light emitting diodes 18 (CR3 and CR4) is established by resistor R1, which in the preferred embodiment has a value of 110 ohms. Located within the drop detector housing itself will be the components contained with dashed line 34 in FIG. 5. Specifically, light emitting diodes 18 (CR3 and CR4) and phototransistors 20 (Q2 and Q3). It has been found that selecting light emitting diodes (CR3 and CR4) which have a beam angle of about 50° will provide sufficient light coverage for the interior 62 of housing 50. In the preferred embodiments light emitting diodes bearing part No. TIL-38 and manufactured by Texas Instruments are employed.

Series-connected phototransistors 20 (Q2 and Q3) are selected so that they will conduct electricity in an amount directly proportional to the light energy which falls upon their surface. Q2 and Q3 are connected in reversed bias, zener mode, to increase their resistance change with varying light intensity and thus produce a greater output voltage than they would if connected in forward bias mode. In low ambient light conditions a drop falling through the light beam produced by light emitting diodes 18 will cause a shadow to pass over either or both phototransistors 20 (Q2 or Q3). The shadow will cause the conductivity of phototransistor 20 (Q2 and Q3) to decrease. This decrease in conductivity will cause a positive voltage pulse to be produced by the phototransistors 20 (Q2 and Q3). The value of this positive voltage pulse 30 is tailored by R3 which, in the preferred embodiment, has been selected to have a value of 270 K ohms. Resistor R3 is in turn connected to a power supply which in the preferred embodiment has a value of 5 volts.

In high ambient light conditions, a different mode of operation takes place. Ambient light is reflected from the surface of the falling drop 28 (FIG. 3). This reflection causes an increase in the amount of light falling on one or both phototransistors 20 (Q2 or Q3). This increase in light energy falling on the surface of phototransistor 20 causes an increase in conductivity of phototransistors 20 (Q2 and Q3). The increased conductivity results in a negative voltage pulse being produced. As with the positive voltage pulse the negative voltage pulse is tailored by R3 before it is electrically conducted to integrator circuit 22. In the preferred embodiment phototransistors 20 bearing part No. TIL-414 manufactured by Texas Instruments are employed.

Integrator circuit 22 is formed by connecting capacitor C4 in series with a network formed by the parallel connection of capacitor C2 and R21. In the preferred embodiment capacitor C4 has a value of 0.1 microfarads, C2 has a value of 0.01 microfarads and resistor R21 has a value of 10 K ohms.

A reference voltage is supplied to the comparator circuit 24 by the interaction of diodes CR1, CR2 and resistor R2. Diodes CR1 and CR2 are each designated as N914A diodes in the preferred embodiment and resistor R2 is selected to have a value of 100 K ohms.

When a drop is not falling in drip chamber 10 the voltage received at comparator 24 from integrator circuit 22 is slightly less than reference voltage 26 because of the bias provided by resistor R21. When a drop falls through drip chamber 10, the voltage received by comparator 24 (AR1) from integrator circuit 22 is greater than reference voltage 26 and causes the output of comparator 24 to fall to a low level. This reduction to a low level of electrical output is sent to a counting and recording microprocessor (not shown) which registers the falling of a drop. As drop formers are designed to form drops of a specific volume, the counting of drops having a known value can be extrapolated into the measurement of either fluid flow or fluid volume or detection of occluded tubing. These parameters can then be displayed on the face of flow control device 99.

Figure 6:
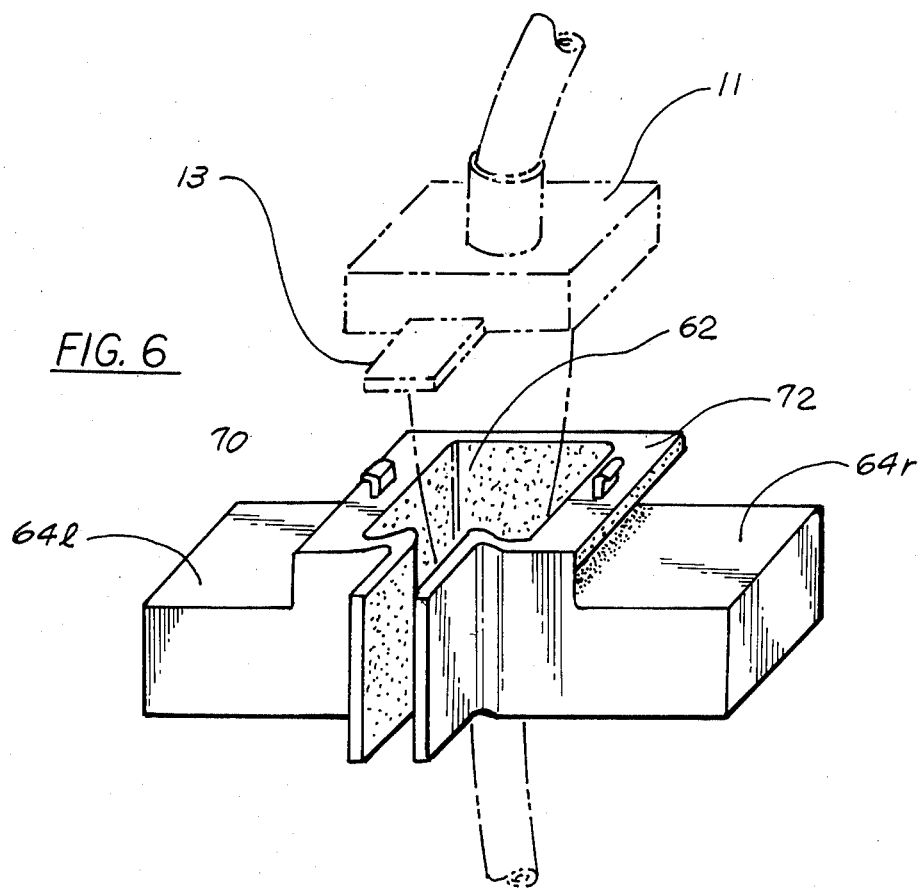
FIG. 6 is a perspective view of the housing used with the present invention.

As can be seen in FIGS. 1, 6 and 7 housing 50 is shaped so as to minimize the passage of light into space 62 which is provided for the mounting of translucent drip chamber 10. As best shown in FIG. 7 shutters 14 and 16 restrict the angle at which the light rays L may enter space 62. Rounded portions 66 further restrict the path of reflected light rays. Shade 12 when in place over shutters 14 and 16 still further blocks the light which would enter space 62 from above. The top 11 of drip chamber 10 is positioned with respect to housing 50 by ears 70 which protrude from its upper surface 72. It has been found that fabricating housing 50 from a material colored a dark color, such as black, will further enhance the ability to the drop detecting system to sense falling drops.

In this manner the drop detecting system of the present invention is able to detect the presence of falling drops irrespective of ambient light conditions. Additionally it will detect the presence of a falling drop even if the translucent drip chamber 10 is tilted out of position.

The foregoing invention can now be practiced by those skilled in the art. Such skilled persons will know that the invention is not necessarily restricted to the embodiments presented herein. The scope of the invention is to be defined by the terms of the following claims, as given meaning by the preceding description.

I claim:

1. A system for detecting the occurrence of drops of falling fluid under different ambient light conditions, comprising:
   (a) a drip chamber through which said drops fall in a substantially straight path;
   (b) light emission means, located in said chamber on one side of said path, for producing a beam of light adapted to intersect said path;
   (c) light responsive means, located in said chamber on another side of said path, for receiving said beam; and
   (d) circuit means, coupled to said light responsive means, causing production of a first signal of one polarity when said beam is intercepted by one of said drops under a first ambient light condition, and causing production of a second signal of opposite polarity by reflecting ambient light off of one of said drops and onto said light responsive means under a second ambient light condition characterized by more ambient light than said first condition, whereby said first signal is indicative of the occurrence of one of said falling drops under said first condition, and said second signal is indicative of the occurrence of one of said falling drops under said second condition.

2. The system defined in claim 1 wherein said light responsive means comprises a pair of photo elements in electical series connection.

3. The system defined in claim 1 wherein said drip chamber has a shade mounted thereto and baffles located at opposite sides of said drip chamber for blocking ambient light.

4. The system defined in claim 1 wherein said light emission means are light emitting diodes and said light responsive means are phototransistors.

5. A system for detecting the occurrence of drops of falling fluid under different ambient light conditions, comprising:
   (a) a drip chamber through which said drops fall in a substantially straight path;
   (b) light emission means, located in said chamber on one side of said path, for producing a beam of light adapted to intersect said path;
   (c) light responsive means including a pair of serially coupled photo elements, one of said photo elements being located on the other side of said chamber along a first line extending from said light emission means through said path, and the other of said photo elements also being located on the other side of said chamber along a different line extending from said emission means through said path, each of said photo elements being adapted to receive at least a portion of said beam; and
   (d) circuit means, coupled to said photo elements, causing production of a first signal of one polarity when said beam is intercepted by one of said drops under a first ambient light condition, and causing production of a second signal of opposite polarity by reflecting ambient light off of one of said drops and onto said light responsive means under a second ambient light condition characterized by more ambient light than said first condition, whereby said first signal is indicative of the occurrence of one of said falling drops under said first condition, and said second signal is indicative of the occurrence of one of said falling drops under said second condition.

6. A system for detecting the occurrence of drops of falling fluid under different ambient light conditions, comprising:
   (a) a drip chamber through which said drops fall in a substantially straight path;
   (b) light emission means, located in said chamber on one side of said path, for producing a beam of light adapted to intersect said path;
   (c) light responsive means including a pair of serially coupled photo elements, one of said photo elements being located on the other side of said chamber along a first line extending from said light emission means through said path and the other of said photo elements also being located on the other side of said chamber along a different line extending from said emission means through said path, each of said photo elements being adapted to receive at least a portion of said beam;
   (d) circuit means, coupled to said photo elements, causing production of a first signal of one polarity when said beam is intercepted by one of said drops under a first ambient light condition, and causing production of a second signal of opposite polarity by reflecting ambient light off of one of said drops and onto said light responsive means under a second ambient light condition characterized by more ambient light than said first condition;
   (e) integration means, coupled to said photo elements, for producing an integrated signal upon receipt of said first signal or said second signal; and
   (f) comparator means, coupled to said integration means, for producing an output signal indicative of the occurrence of one of said falling drops when said integrated signal applied to said comparator means differs by a pre-determined amount from a reference signal also applied thereto.

7. A system for detecting falling drops of fluid comprising:
   (a) a drip chamber through which said drops fall in a substantially straight path, said drip chamber having an opening therein;
   (b) light emission means, located in said chamber on one side of said path, for producing a beam of light adapted to intersect said path;
   (c) light responsive means including a pair of serially coupled photo elements, one of said photo elements being located on the other side of said chamber along a first line extending from said light emission means through said path and the other of said photo elements also being located on the other side of said chamber along a different line extending from said emission means through said path, each of said photo elements being adapted to receive at least a portion of said beam;
   (d) a shade mounted to said drip chamber above said opening and a pair of baffles located at opposite sides of said opening, said shade and said baffles substantially blocking ambient light from entering said drip chamber through said opening under a first ambient light condition, and for permitting ambient light to enter said drip chamber through said opening under a second ambient light condition characterized by more ambient light than said first condition;
   (e) circuit means, coupled to said light responsive means, for producing a first signal when, in the presence of a first ambient light condition, said beam is intercepted by one of said falling drops, and for producing a second signal when, in the presence of a second ambient light condition, ambient light enters said chamber through said opening and is reflected off of one of said falling drops and onto said light responsive means, whereby the presence of either said first or said second signal is indicative of the occurrence of one of said falling drops.

8. A system for detecting the occurrence of drops of falling fluid comprising:
   (a) a drip chamber through which said drops fall in a substantially straight path, said drip chamber having a shade mounted thereto and baffles located at opposite sides of said drip chamber for blocking ambient light;
   (b) light emission means, located in said chamber on one side of said path, for producing a beam of light adapted to intersect said path;
   (c) a pair of serially coupled photo elements, one of said photo elements being located on the other side of said chamber along a first line extending from said light emission means through said path, and the other of said photo elements also being located on the other side of said chamber along a different line extending from said emission means through said path, each of said photo elements being adapted to receive at least a portion of said beam;
   (d) circuit means coupled to said photo elements, causing production of a first signal when said beam is intercepted by one of said drops, and causing production of a second signal by reflecting ambient light, not blocked by said shade or said baffles, off of one of said drops and onto at least one of said photo elements:
   (e) integration means, coupled to said circuit means, adapted to produce an integrated signal upon receipt of said first signal or said second signal;
   (f) generation means for generating a predetermined reference signal; and
   (g) comparator means, having a first input coupled to said integration means for receiving said integrated signal, and a second input coupled to said generation means for receiving said reference signal; said comparator means producing an output signal indicative of the occurrence of a falling drop when said integrated signal differs from said reference signal by a predetermined amount.

* * * * *